United States Patent [19]
Hall et al.

[11] Patent Number: 5,932,228
[45] Date of Patent: *Aug. 3, 1999

[54] DERMATOLOGICAL COMPOSITIONS AND METHOD OF TREATMENT OF SKIN LESIONS THEREWITH

[75] Inventors: Bonnie Joy Hall, Mason; Julie Anne Baur, Fairfield; George Endel Deckner, Cincinnati, all of Ohio

[73] Assignee: The Procter & Gamble Company, Cincinnati, Ohio

[*] Notice: This patent is subject to a terminal disclaimer.

[21] Appl. No.: 08/652,083

[22] Filed: May 23, 1996

Related U.S. Application Data

[63] Continuation of application No. 08/457,545, Jun. 1, 1995, Pat. No. 5,545,407, which is a continuation of application No. 08/326,446, Oct. 20, 1994, Pat. No. 5,445,823.

[51] Int. Cl.$^6$ ..................................................... A61K 7/48
[52] U.S. Cl. ..................... 424/401; 514/859; 514/864; 514/944
[58] Field of Search .................... 424/401; 514/859, 514/944, 864

[56] References Cited

U.S. PATENT DOCUMENTS

| | | | |
|---|---|---|---|
| 5,545,545 | 8/1996 | Hall et al. | 424/401 |
| 5,681,852 | 10/1997 | Bissett | 514/556 |

FOREIGN PATENT DOCUMENTS

| | | | |
|---|---|---|---|
| 61-12618 | 1/1986 | Japan . | |

*Primary Examiner*—Jyothsna Venkat
*Attorney, Agent, or Firm*—Loretta J. Henderson; George W. Allen

[57] ABSTRACT

The present invention relates to compositions for treating acne and other skin lesions and also to methods of treatment utilizing these compositions. These compositions and methods of treatment employ benzoyl peroxide, a compound for reducing the skin irritation associated therewith, and a topical carrier.

10 Claims, No Drawings

5,932,228

DERMATOLOGICAL COMPOSITIONS AND METHOD OF TREATMENT OF SKIN LESIONS THEREWITH

This is a continuation of application Ser. No. 08/457,545 filed on Jun. 1, 1995, now U.S. Pat. No. 5,545,407, which is a continuation of application Ser. No. 08/326,446, filed on Oct. 20, 1994 which issued as U.S. Pat. No. 5,445,823 on Aug. 29, 1995.

TECHNICAL FIELD

The present invention relates to dermatological compositions for treating acne and other skin lesions in humans. The invention also relates to methods of treatment utilizing these compositions. These compositions and methods of treatment comprise a therapeutically effective amount of benzoyl peroxide, an effective amount of a compound for reducing the redness and skin irritation associated with the benzoyl peroxide selected from the group consisting of panthenol, pantothenic acid, pantetheine, pantethine, C1–C30 alkyl esters of panthothenic acid, C1–C30 carboxylic acid esters of panthenol, C1–C30 alkyl ethers of panthenol, tocopherol, C1–C30 carboxylic acid esters of tocopherol, zinc oxide, allantoin, and mixtures thereof, and a topical carrier.

BACKGROUND OF THE INVENTION

Acne is a condition of the human skin characterized by an excess flow of sebum, or skin oil, from the sebaceous glands located in the pilosebaceous apparatus. Sebum reaches the skin surface through the duct of the hair follicle. The presence of excessive amounts of sebum in the duct and on the skin acts to block or stagnate the continuous flow of sebum from the follicular duct, thus producing a thickening and a solidification of the sebum to form a solid plug known as a comedone. When this process occurs, hyperkeratinization of the follicular opening is stimulated, thus completely closing the duct. The usual results are papules, pustules, or cysts, often contaminated with bacteria which cause secondary infections. Acne is particularly characterized by the presence of comedones, inflammatory papules, pustules, or cysts. The effect of acne ranges from slight skin irritation and pitting to disfiguring scars.

Many topical therapeutic agents are employed in the treatment of acne and seborrhea to prevent the blocking of the follicular duct, to reopen the duct once it has become blocked, to act against the infecting bacteria or the thickened sebum, and to provide combinations of each of these actions. The horny outer layer of the skin, which is known as the stratum corneum, is formed of dead cells composed largely of keratin. Therapeutic agents which act to prevent the blocking of the follicular duct by promoting the removal or sloughing off of excess keratin are known as keratolytic agents.

Benzoyl peroxide has been used as a keratolytic agent and an antibacterial agent in the topical treatment of skin lesions such as acne, seborrhea, burns, varicose ulcers, skin irritations, and sycosis vulgaris. See e.g., Levine et al., *Ohio State Med. J.*, 65, 492 (1969); U.S. Pat. No. 3,535,422, to Cox et al., issued Oct.20, 1970; British Patent Application Nos. 1,185,685, to Fisher, published Mar. 25, 1970; 1,163, 004, to Stiefel Laboratories, Inc., published Sep. 4, 1969; and 1,407,937, to Stiefel Laboratories, Inc. published Oct. 1, 1975. As noted, benzoyl peroxide has been used as a very effective keratolytic and antibacterial agent in the treatment of acne. The topical application of benzoyl peroxide for skin lesion therapy is thoroughly detailed in the medical literature. See Brogdne et al., *Drugs*, 4, 417 (1974); Poole et al., *Arch Derm.*, 102, 400 (1972); Eaglstein, *Arch Derm.*, 97, 527 (1968); Pace, *Can Med. Assoc. J.*, 93,252 (1965); Vasarinsh, *Arch. Derm.*, 98, 183 (1968); Mysliborski et al., *AFP*, 15, 86 (1977); Nare, *Br. J. Clin. Prac.*, 29, 63 (1975); Fulton et al., *Arch. Derm.*, 1, 10, 83 (1974); and Wilkinson et al., *Can. Med. Assoc. J.*, 95, 28 (1966).

While benzoyl peroxide is an effective topical agent for the treatment of skin lesions such as appear in acne, seborrhea, and other conditions, it has the undesirable side effect of being a contact irritant. The irritation associated with benzoyl peroxide therapy has also been detailed in the medical literature cited in the previous paragraph. Additionally, the redness induced by benzoyl peroxide may impair a patient's ability to perceive the improvement in acne condition initially. Accordingly, some patients are denied the benefits of benzoyl peroxide therapy because of the irritation problem. When used in the treatment of acne, benzoyl peroxide produces dryness, exfoliation, increased redness and a decrease in bacterial flora.

It has been surprisingly found in the present invention that highly efficacious compositions which are non-irritating or less irritating to the skin are achieved when the benzoyl peroxide is utilized in conjunction with at least one other compound selected from the group consisting of panthenol, pantothenic acid, pantotheine, pantothine, C1–C30 alkyl esters of panthothenic acid, C1–C30 carboxylic acid esters of panthenol, C1–C30 alkyl ethers of panthenol, tocopherol, C1–C30 carboxylic acid esters of tocopherol, zinc oxide, allantoin, and mixtures thereof. Because these compositions are non-irritating or less irritating to the skin and reduce skin redness, these compositions have the advantage of inducing compliance to a treatment regimen. Consequently, because of the higher likelihood of user compliance, there is increased likelihood of successful treatment of the acne or other skin lesions.

It is therefore an object of the present invention to provide dermatological compositions for the treatment of acne and other skin lesions in humans.

It is another object of the present invention to provide dermatological compositions for the treatment of acne and other skin lesions in humans which are non-irritating or less irritating, and reduce redness better, than benzoyl peroxide alone.

It is another object of the present invention to provide methods for the treatment of acne and other skin lesions in humans.

It is another object of the present invention to provide methods of the treatment of acne and other skin lesions in humans whereby the methods are non-irritating or less irritating to the user, and reduce redness better, than benzoyl peroxide alone.

These and other objects of this invention will become apparent in light of the following disclosure.

SUMMARY OF THE INVENTION

The present invention relates to a dermatological composition for treating skin lesions comprising:

(a) a therapeutically effective amount of benzoyl peroxide, (b) an effective amount of a compound for reducing the skin irritation associated with the benzoyl peroxide selected from the group consisting of panthenol, pantothenic acid, pantetheine, pantethine, C1–C30 alkyl esters of pantothenic acid, C1–C30 carboxylic acid esters of panthenol, C1–C30 alkyl ethers of panthenol, tocopherol, C1–C30 carboxylic acid esters of tocopherol, zinc oxide, allantoin, and mixtures thereof, and (c) a topical carrier.

The present invention also relates to methods of treatment of skin lesions utilizing these compositions.

All percentages and ratios used herein are by weight of the total composition and all measurements made are at 25° C., unless otherwise designated. All weight percentages, unless otherwise indicated, are on an actives weight basis. The invention hereof can comprise, consist of, or consist essentially of, the essential as well as optional ingredients and components described herein.

DETAILED DESCRIPTION OF THE INVENTION

It has been found that the combination of benzoyl peroxide and one or more compounds selected from the group consisting of panthenol, pantothenic acid, pantetheine, pantethine, C1–C30 alkyl esters of pantothenic acid, C1–C30 carboxylic acid esters of panthenol, C1–C30 alkyl ethers of panthenol, tocopherol, C1–C30 carboxylic acid esters of tocopherol, zinc oxide, allantoin, and mixtures thereof, are highly efficacious for the treatment of acne and other skin lesions and have the advantage of not suffering from the highly irritating effects often produced by benzoyl peroxide alone.

As used herein the term "dermatological composition" means a composition useful for topical application to the skin of a human.

The term "topical application", as used herein, means to apply or spread the compositions of the present invention to the surface of the skin.

As used herein the term "therapeutically effective amount" means an amount of the benzoyl peroxide sufficient to reduce or ameliorate acne or other skin lesions in humans and the effects associated therewith, including, but not limited to, inflammation, irritation, peeling flaking, and the like.

As used herein the term "an effective amount of a compound for reducing the skin irritation associated with the benzoyl peroxide" means an amount of such a compound, as described herein, that is sufficient to reduce or ameliorate the irritation, redness, and other adverse effects associated with the use of benzoyl peroxide. These other adverse effects can include, but are not limited to, inflammation, itching, peeling, burning, erythema, and the like.

The term "pharmaceutically-acceptable", as used herein, means that the compositions or components thereof so described are of sufficiently high purity and suitable for use in contact with human skin without undue toxicity, incompatibility, instability, allergic response, and the like.

Benzoyl Peroxide

An essential component of the compositions of the present invention is benzoyl peroxide, which is also known as dibenzoyl peroxide. Without being limited by theory, it is believed that benzoyl peroxide provides its anti-acne and anti-skin lesion effects because of its keratolytic properties, and also because of its anti-microbial and oxidizing properties. Benzoyl peroxide is described in *The Merck Index*, Tenth Edition, entry 1119, p. 1122 (1983) and 56 *Federal Register*, pp. 41008–20, Aug. 16, 1991, both of these references being incorporated herein by reference in their entirety.

A wide range of benzoyl peroxide concentrations can be utilized in the present invention depending upon a number of factors including, but not limited to, the choice of topical carrier, the severity of the acne or skin lesions to be treated, the duration of treatment, etc. The compositions of the present invention comprise a therapeutically effective amount of the benzoyl peroxide for the treatment of acne and other skin lesions. The compositions of the present invention typically comprise from about 0.1% to about 20%, more preferably from about 2.5% to about 10%, and most preferably from about 2.5% to about 5% of benzoyl peroxide, based on the weight of the total composition.

Compounds for Reducing the Skin Irritation Associated with Benzoyl Peroxide

The compositions of the present invention also comprise one or more compounds for reducing the skin irritation associated with the benzoyl peroxide. These compounds are selected from the group consisting of panthenol, pantothenic acid, pantetheine, pantethine, C1–C30 alkyl esters of pantothenic acid, C1–C30 carboxylic acid esters of panthenol, C1–C30 alkyl ethers of panthenol, tocopherol, C1–C30 carboxylic acid esters of tocopherol, zinc oxide, allantoin, and mixtures thereof.

A wide range of concentrations of these compounds can be utilized in the present invention depending upon a number of factors including, but not limited to, the choice of topical carrier, the level of benzoyl peroxide chosen, the severity of the acne or skin lesions, the duration of treatment, etc. The compositions of the present invention comprise an effective amount of one or more of these compounds for reducing the skin irritation associated with the benzoyl peroxide. The compositions of the present invention typically comprise in total from about 0.05% to about 20%, more preferably from about 0.1% to about 10%, and most preferably from about 0.5% to about 5%, of one or more of these compounds, based on the weight of the total composition.

Panthenol, Panthenol Esters, and Panthenol Ethers

Panthenol is the alcohol corresponding to pantothenic acid, the acid being a member of the B complex vitamins. Panthenol is also known as pantothenol and 2,4-dihydroxy-N-(3-hydroxypropyl)-3,3-dimethylbutanamide. The material can exist as stereoisomers, e.g., the D(+) form, the L(−) form, the racemate, and other mixtures of the D(+) and L(−) forms. The D(+) form, which is also known as dexpanthenol, is related to the naturally occurring pantothenic acid. In the present invention, the term "panthenol" when used herein includes the D(+) form, the L(−) form, the racemate, and other mixtures of the D(+) and L(−) forms, unless otherwise specified.

Also useful herein are C1–C30 carboxylic acid esters of panthenol, i.e. a C1–C30 carboxylic acid which has been esterified with panthenol. These carboxylic acid esters include esters derived from straight chain carboxylic acids, branched chain carboxylic acids, and cyclic carboxylic acids, as well as the corresponding unsaturated carboxylic acids. These esters also include diesters and triesters of panthenol. Nonlimiting examples of panthenol esters include panthenyl acetate, panthenyl proprionate, panthenyl butyrate, panthenyl stearate, panthenyl 2-cyclohexylacetate, panthenyl isobutyrate, panthenyl linoleate, panthenyl triacetate, and mixtures thereof.

Also useful herein are C1–C30 alkyl ethers of panthenol. These ethers include straight chain ethers, branched chain ethers, and cyclic ethers, as well as the corresponding unsaturated ethers. A particularly preferred ether is panthenyl ethyl ether.

In addition to the C1–C30 alkyl esters and alkyl ethers described above, mixed alkyl esters and ethers such as panthenyl ethyl ether acetate are also useful herein.

Pantothenic Acid, Pantothenic Acid Esters, Pantetheine, and Pantethine

Pantothenic acid is a member of the B complex vitamins and is also known as N-(2,4-dihydroxy-3,3-dimethylbutyryl)-β-alanine and vitamin $B_3$. The material can exist as stereoisomers, e.g., the D(+) form, the L(−) form, the racemate, and other mixtures of the D(+) and L(−) forms. The D(+) form, is the naturally occurring form. In the present invention, the term "pantothenic acid" when used herein includes the D(+) form, the L(−) form, the racemate, and other mixtures of the D(+) and L(−) forms, unless otherwise specified. Pantothenic acid is described in *The Merck Index*, Tenth Edition, entry 6877, p. 1007 (1983), which is incorporated herein by reference in its entirety.

Also useful herein are C1–C30 alkyl esters of pantothenic acid, i.e. pantothenic acid which was been esterified with a C1–C30 alcohol. These pantothenic acid esters include esters derived from straight chain alcohols, branched chain alcohols, and cyclic alcohols, as well as the corresponding unsaturated esters. Nonlimiting examples of these esters include methyl pantothenate, ethyl pantothenate, propyl pantothenate, isobutyl pantothenate, 2-ethylhexyl pantothenate, cetyl pantothenate, lauryl pantothenate, stearyl pantothenate, cyclohexyl pantothenate, and mixtures thereof.

Pantetheine is the thiol compound related to panthenol and pantothenic acid, corresponding to the chemical formula $C_{11}H_{22}N_2O_4S$. Pantetheine is described in *The Merck Index*, Tenth Edition, entry 6873, p. 1006 (1983), which is incorporated herein by reference in its entirety.

Pantethine is the disulfide compound, which is a dimer of pantetheine, corresponding to the chemical formula $C_{22}H_{44}N_4O_8S_2$. Pantethine acid is described in *The Merck Index*, Tenth Edition, entry 6874, p. 1006 (1983), which is incorporated herein by reference in its entirety.

Tocopherol and Tocopheryl Esters

Tocopherol is a member of the vitamin E family. Various forms of tocopherol or vitamin E are known including the α (alpha), β (beta), γ (gamma), δ (delta), ε (epsilon), and ζ (zeta) forms. See *The Merck Index*, Tenth Edition, (1983), entries 9322, 9323, 9324, 9325, 9326, 9327, 9328, 9329, 9832, and 9833, all of which are incorporated by reference herein in their entirety. The term "tocopherol", as used herein is understood to encompass all of these forms of tocopherol, unless otherwise specified.

Also useful herein are C1–C30 carboxylic acid esters of any of these tocopherol materials, i.e. a C1–C30 carboxylic acid which has been esterified with a tocopherol. These carboxylic acid esters include esters derived from straight chain carboxylic acids, branched chain carboxylic acids, and cyclic carboxylic acids, as well as the corresponding unsaturated carboxylic acids. Nonlimiting examples of these esters include tocopheryl acetate, tocopheryl proprionate, tocopheryl butyrate, tocopheryl stearate, tocopheryl 2-cyclohexylacetate, tocopheryl isobutyrate, tocopheryl linoleate, tocopheryl sorbate, and mixtures thereof. Particular preferred carboxylic acid esters of tocopherol include tocopheryl acetate and tocopheryl sorbate.

Also useful herein are other tocopherol derivatives such as tocopheryl monoesters of difunctional acids, e.g. tocopheryl acid succinate, and ethoxylated and propoxylated derivatives of these monoesters, e.g. tocopheryl polyethylene glycol 1000 succinate (i.e. wherein the succinic acid is esterified with the tocopherol on one acid functional group and with the ethylene glycol on the other acid functional group.)

Also useful herein are compounds related to the tocopherols such as Trolox C, which has the chemical name 6-hydroxy-2,5,7,8-tetramethylchroman-2-carboxylic acid. See U.S. Pat. No. 4,847,267, to Deckner et al., issued Jul. 11, 1989, which is incorporated by reference herein in its entirety, and which discloses these compounds.

Zinc Oxide

Zinc oxide is a material which is generally represented by the chemical formula ZnO. Zinc Oxide is described in *The Merck Index*, Tenth Edition, entry 9952, p. 9961 (1983), which is incorporated herein by reference in its entirety. This material is a white or yellowish white powder.

Allantoin

Allantoin is also known as (2,5-dioxo-4-imidazolidinyl) urea and corresponds to the chemical formula $C_4H_6N_4O_3$. Allantoin is described in *The Merck Index*, Tenth Edition, entry 242, p. 243 (1983), which is incorporated herein by reference in its entirety.

Other Compounds

In addition to the compounds described above for reducing the skin irritation associated with benzoyl peroxide, other compounds are also useful herein provided they meet the criteria of having anti-oxidant properties and of having a weighted arithmetic mean solubility parameter below about 7, preferably from about 5 to about 6.5, and most preferably from about 5 to about 6. Solubility parameters are well known to the formulation chemist of ordinary skill in the art and are routinely used as a guide for determining compatibility's and solubilities of materials in the formulation process. Without being limited by theory, it is believed that by choosing an antioxidant having a low solubility parameter, that the antioxidant will have appreciable solubility in the naturally occurring skin lipids, e.g. squalene, such that the antioxidant can help to prevent the oxidation of these lipids by the benzoyl peroxide active to form lipid peroxidation compounds which can be irritating to the skin. See C. Colin et al., "Non Invasive Methods Of Evaluation Of Oxidative Stress Induced By Low Doses Of Ultra Violet In Humans", 50–72, *IFSCC*, Venezia, which is incorporated by reference herein in its entirety.

The solubility parameter of a chemical compound, δ, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[\frac{\sum_i E_i}{\sum_i m_i}\right]^{1/2}$$

wherein $\Sigma_i E_i$=the sum of the heat of vaporization additive group contributions, and $\Sigma_i m_i$=the sum of the molar volume additive group contributions Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics,* 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

$$1\ J/mol = 0.239006\ cal/mol\ \text{and}\ 1000\ J = 1\ kJ.$$

See Gordon, A. J. et al., *The Chemist's Companion,* John Wiley & Sons, pp. 456–463, (1972), which is incorporated by reference herein in its entirety.

Solubility parameters have also been tabulated for a wide variety of chemical materials. Tabulations of solubility parameters are found in the above-cited *Handbook of Solubility Parameters.*

Topical Carrier

The compositions of the present invention also comprise a topical carrier. The term "topical carrier", as used herein, is well-known to one of ordinary skill in the art, and means one or more compatible solid or liquid filler diluents or vehicles which are suitable for administration to a human. The term "compatible", as used herein, means that the components of the dermatological compositions are capable of being comingled with the components of the present invention, and with each other, in a manner such that there is no interaction which would substantially reduce the therapeutic efficacy of the composition under ordinary use situations. The topical carrier must be a pharmaceutically acceptable carrier. The term "pharmaceutically-acceptable", as used herein, means that the topical carrier must be of sufficiently high purity and suitable for use in contact with human skin without undue toxicity, incompatibility, instability, allergic response, and the like.

The dermatological compositions of the subject invention are administered topically to a biological subject, i.e., by the direct laying on or spreading of the composition on the skin of the subject. The topical compositions useful in the subject invention involve compositions suitable for topical application to human skin.

The topical compositions useful in the subject invention can be made into a wide variety of product types. These include, but are not limited to, lotions, creams, gels, sticks, sprays, ointments, pastes, mousses, and cosmetics. These product types can comprise several types of carrier systems including, but not limited to solutions, emulsions, gels, solids, and liposomes. Also useful are cleansing compositions which also deliver the components of the present invention to the skin during the cleansing process.

The topical compositions useful in the subject invention formulated as solutions typically include a pharmaceutically-acceptable aqueous or organic solvent. Water is a preferred solvent. Examples of suitable organic solvents include: ethanol, propylene glycol, polyethylene glycol, polypropylene glycol, glycerol, 1,2,4-butanetriol, sorbitol esters, 1,2,6-hexanetriol, ethanol, isopropanol, sorbitol esters, butanediol, and mixtures thereof. These solutions useful in the subject invention preferably contain from about 80% to about 99.99% of an acceptable aqueous or organic solvent.

If the topical compositions useful in the subject invention are formulated as an aerosol and applied to the skin as a spray-on, a propellant is added to a solution composition. Examples include chloro-fluorinated lower molecular weight hydrocarbons. A more complete disclosure of propellants useful herein can be found in Sagarin, *Cosmetics Science and Technology,* 2nd Edition, Vol. 2, pp. 443–465 (1972), which is incorporated herein by reference in its entirety.

Topical compositions useful in the subject invention can be formulated as a solution comprising an emollient. Such compositions preferably contain from about 2% to about 50% of a topical pharmaceutically-acceptable emollient.

As used herein, "emollient" refers to materials used for the prevention or relief of dryness, as well as for the protection of the skin. A wide variety of suitable emollients are known and can be used herein. See e.g., Sagarin, *Cosmetics, Science and Technology,* 2nd Edition, Vol. 1, pp. 32–43 (1972), and U.S. Pat. No. 4,919,934, to Deckner et al., issued Apr. 24, 1990, both of which are incorporated herein by reference in their entirety.

A lotion can be made from a solution carrier system. Lotions typically comprise from about 1% to about 20%, preferably from about 5% to about 10%, of an emollient; and from about 50% to about 90%, preferably from about 60% to about 80%, water.

Another type of product that can be formulated from a solution carrier system is a cream. A cream typically comprises from about 5% to about 50%, preferably from about 10% to about 20%, of an emollient, and from about 45% to about 85%, preferably from about 50% to about 75%, water.

Yet another type of product that can be formulated from a solution carrier system is an ointment. An ointment can comprise a simple base of animal or vegetable oils or semi-solid hydrocarbons (oleaginous). Ointments can also comprise absorption ointment bases which absorb water to form emulsions. Ointment carriers can also be water soluble. An ointment can comprise from about 2% to about 10% of an emollient; and from about 0.1% to about 2% of a thickening agent. A more complete disclosure of thickening agents useful herein can be found in Sagarin, *Cosmetics, Science and Technology.* 2nd Edition, Vol. 1, pp. 72–73 (1972), which has been incorporated by reference herein in its entirety.

If the carrier is formulated as an emulsion, preferably from about 0.1% to about 10%, more preferably from about 0.5% to about 2%, of the carrier system comprises an emulsifier. Emulsifiers can be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers,* North American Edition, pages 317–324 (1986), all of these references being incorporated herein by reference in their entirety. Various emulsion topical carriers, as well as other topical carriers, are also described in U.S. Pat. No. 5,306,485, to Robinson et al., issued Apr. 26, 1994, which is incorporated by reference herein in its entirety.

The cleaning compositions useful in the subject invention preferably contain from about 1% to about 90%, more preferably from about 5% to about 10%, of a cosmetically-acceptable surfactant.

The physical form of the cleansing compositions is not critical. The compositions can be, for example, formulated as toilet bars, liquids, shampoos, pastes, or mousses. Rinse-off cleansing compositions, such as shampoos, require a delivery system adequate to deposit sufficient levels of actives on the skin and scalp. A preferred delivery system involves the use of insoluble complexes. For a more complete disclosure, see U.S. Pat. No. 4,835,148, Barford et al., issued May 30, 1989; incorporated herein by reference in its entirety.

The cleaning compositions useful in the subject invention can optionally contain, at their art-established levels, materials which are conventionally used in cleansing compositions. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, *Detergents and Emulsifiers,* North American Edition (1986), published by Allured Publishing Corporation, which is incorporated herein by reference in its entirety.

Additional Components

The compositions of the present invention can comprise a wide range of additional components. The *CTFA Cosmetic Ingredient Handbook,* Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers,, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, surfactants (cleansing agents, emulsifying agents, foam boosters, hydrotropes, solubilizing agents, and suspending agents), suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include emulsifiers, solubilizing agents, sequestrants, and keratolytics, and the like.

Nonlimiting examples of these additional components cited in the *CTFA Cosmetic Ingredient Handbook,* as well as other materials useful herein, include the following: vitamins and derivatives thereof [e.g., vitamin C, Vitamin A (i.e. retinoic acid), retinol, retinoids, and the like]; sunscreening agents (nonlimiting examples of sunscreening agents are disclosed in U.S. Pat. No. 5,219,558, to Woodin, Jr. et al., issued Jun. 15, 1993, which is incorporated herein by reference in its entirety); silicones (e.g., dimethicone, cyclomethicones, dimethiconol, dimethicone copolyol, phenyl dimethicones, amodimethicones, and the like); antioxidants; anti-microbial agents; preservatives; emulsifiers; polyethyleneglycols and polypropyleneglyocls; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; other anti-acne medicaments (e.g., resorcinol, sulfur, salicylic acid, erythromycin, zinc, and the like); skin bleaching (or lightening) agents including but not limited to hydroquinone, kojic acid; antioxidants; chelators and sequestrants; thickening agents such as carbomers (homopolymers of acrylic acid crosslinked with an allyl ether of pentaerythritol or an allyl ether of sucrose), acrylates/C10–30 alkyl acrylate crosspolymers (e.g., copolymers of C10–30 alkyl acrylates and one or more monomers of acrylic acid, methacrylic acid or one of their simple esters crosslinked with an allyl ether of sucrose or an allyl ether of pentaerythritol), crosslinked and non-crosslinked nonionic and cationic polyacrylamides [e.g., Salcare SC92 which has the CTFA designation polyquaternium 32 (and) mineral oil, and Salcare SC 95 which has the CTFA designation polyquaternium 37 (and) mineral oil (and) PPG-1 trideceth-6, and the nonionic Seppi-Gel polyacrylamides available from Seppic Corp.]; aesthetic components such as fragrances, pigments, colorings, essential oils, skin senates, astringents, skin soothing agents, skin healing agents and the like, [nonlimiting examples of these aesthetic components include clove oil, menthol, camphor, eucalyptus oil, eugenol, menthyl lactate, witch hazel distillate, bisabolol, dipotassium glycyrrhizinate and the like]; and skin conditioning agents such as urea and glycerol, and also the propoxylated glycerols described in U.S. Pat. No. 4,976,953, to Orr et al., issued Dec. 11, 1990, which is incorporated by reference herein in its entirety.

Methods of Treatment of Acne and Other Skin Lesions

The compositions of the present invention are useful for treating acne and other skin lesions in humans. To obtain a therapeutic benefit a therapeutically effective amount of the compositions of the present invention is applied to the skin.

A wide range of quantities of the compositions of the present invention can be employed to provide a therapeutic anti-acne benefit or a benefit against other skin lesions. Quantities of the present compositions which are typically applied to provide a therapeutic benefit can range from about 0.1 mg/cm$^2$ to about 25 mg/cm$^2$. A particularly useful amount to use is about 2 mg/cm$^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE 1

Anti-Acne Gel

An anti-acne gel is prepared by combining the following ingredients using conventional mixing techniques.

| Ingredients | Weight Percent |
| --- | --- |
| Water | qs 100 |
| Benzoyl Peroxide[1] | 2.50 |
| Carbomer 980[2] | 0.30 |
| Glydant Plus | 0.20 |
| Acrylates/C10–30 Alkylacrylates crosspolymer[3] | 0.05 |
| Disodium EDTA | 0.10 |
| Stearyl Alcohol | 2.25 |
| Cetyl Alcohol | 2.25 |
| Glycerythydroxy Stearate | 0.74 |
| Steareth 100 | 0.50 |
| Dexpanthenol | 5.00 |
| Sodium Hydroxide | 0.05 |

-continued

| Ingredients | Weight Percent |
| --- | --- |
| Dimethicone[4] | 0.60 |
| Cyclomethicone/dimethiconal[5] | 0.50 |

1 Lucidol ® 75 from Elf Atochem, which is a powder containing 75% benzoyl peroxide active.
2 Carbopol ® 980 from B.F. Goodrich.
3 Pemulen ® TR-1 from B.F. Goodrich.
4 Dow Corning ® 200 Fluid (350 centistoke) from Dow Corning.
5 Dow Corning ® Q-2 1401 from Dow Corning.

In a suitable vessel a benzoyl peroxide slurry is prepared by combining the benzoyl peroxide with water which accounts for approximately 3.6% of the batch. This slurry is passed through a Colloid or Urschel mill to disperse the benzoyl peroxide and the mill is rinsed through with an additional 1.44% of water. This rinse is added to the total slurry.

In a separate vessel a 5% sodium hydroxide solution is prepared with water to provide sodium hydroxide to the batch at 0.05%. In another vessel, the carbomer 980 is gradually combined with an amount of water totaling 14.7% of the batch. It is added under agitation to disperse and hydrate the carbomer.

In a suitable mixing tank, the remaining water is added and heated to at least 75° C. In a separate vessel, the dimethicone, cetyl alcohol, stearyl alcohol, glycerylhydroxy stearate, and steareth 100 are added and heated to at least 75° C. As the water phase is heating, the disodium EDTA, glydant plus, and alkyl alkylates are added and mixed until dissolved.

When both phases reach the required temperature, the oil phase is slowly added to the water phase while the entire batch is recycled through a tekmar mill to reduce the oil droplet particle size to approximately one to two microns. The batch is then cooled to room temperature under constant agitation.

When the batch has cooled, the carbopol slurry, benzoyl peroxide slurry, the dexpanthenol which is water soluble, and the cyclomethicone/dimethiconal are added. The batch is again recycled through the tekmar mill to disperse the materials. Finally, the 5% NaOH solution is gradually added with continuous mixing. The composition is then mixed until homogeneous.

The resulting anti-acne composition exhibits low skin irritation and good physical and chemical stability, and is useful for topical application to human skin for the treatment of acne and other skin lesions.

EXAMPLE 2
Anti-Acne Gel

An anti-acne gel is prepared by combining the following ingredients using conventional mixing techniques.

| Ingredients | Weight Percent |
| --- | --- |
| Water | qs 100 |
| Benzoyl Peroxide[1] | 2.50 |
| Glycerin | 3.00 |
| Carbomer 980[2] | 0.30 |
| Glydant Plus | 0.20 |
| Acrylates/C10–30 Alkylacrylates crosspolymer[3] | 0.05 |
| Disodium EDTA | 0.10 |
| Stearyl Alcohol | 2.25 |
| Cetyl Alcohol | 2.25 |
| Glycerylhydroxy Stearate | 0.74 |
| Tocopherol Acetate | 1.00 |

-continued

| Ingredients | Weight Percent |
| --- | --- |
| Steareth 100 | 0.50 |
| Sodium Hydroxide | 0.05 |
| Cyclomethicone/dimethiconal[4] | 1.50 |

1 Lucidol ® 75 from Elf Atochem, which is a powder containing 75% benzoyl peroxide active.
2 Carbopol ® 980 from B.F. Goodrich.
3 Pemulen ® TR-1 from B.F. Goodrich.
4 Dow Corning ® Q-2 1401 from Dow Corning In a suitable vessel a benzoyl peroxide slurry is prepared by combining the benzoyl peroxide with water which accounts for 3.6% of the batch. This slurry is passed through a Colloid or Urschel mill to disperse the benzoyl peroxide and the mill is rinsed through with an additional 1.44% of water. This rinse is added to the total slurry.

In a separate vessel a 5% sodium hydroxide solution is prepared with water to provide sodium hydroxide to the batch at 0.05%. In another vessel the carbomer 980 is gradually combined with an amount of water totaling 14.7% of the batch. It is added under agitation to disperse and hydrate the carbomer.

In a suitable mixing tank, the remaining water is added as well as the glycerin and heated to at least 75° C. In a separate vessel, the cetyl alcohol, stearyl alcohol, glycerylhydroxy stearate, tocopherol acetate and steareth 100 are added and heated to at least 75° C. As the water phase is heating, the disodium EDTA, glydant plus, and alkyl alkylates are added and mixed until dissolved.

When both phases reach the required temperature, the oil phase is slowly added to the water phase while the entire batch is recycled through a tekmar mill to reduce the oil droplet particle size to approximately one to two microns. The batch is then cooled to room temperature under constant agitation.

When the batch has cooled, the carbopol slurry, benzoyl peroxide slurry and the cyclomethicone/dimethiconal is added. The batch is again recycled through the tekmar mill to disperse the materials. Finally, the 5% NaOH solution is gradually added with continuous mixing. The compositions is then mixed until homogeneous.

The resulting anti-acne composition exhibits low skin irritation and good physical and chemical stability, and is useful for topical application to human skin for the treatment of acne and other skin lesions.

EXAMPLE 3
Anti-Acne Gel

An anti-acne gel is prepared by combining the following ingredients using conventional mixing techniques.

| Ingredients | Weight Percent |
| --- | --- |
| Water | qs 100 |
| Benzoyl Peroxide[1] | 2.50 |
| Carbomer 980[2] | 0.30 |
| Glydant Plus | 0.20 |
| Acrylates/C10–30 Alkylacrylates crosspolymer[3] | 0.05 |
| Disodium EDTA | 0.10 |
| Stearyl Alcohol | 2.25 |
| Cetyl Alcohol | 2.25 |
| Tocopherol Acetate | 1.00 |
| Glycerylhydroxy Stearate | 0.74 |
| Steareth 100 | 0.50 |
| Panthenol | 5.00 |
| Allantoin | 0.50 |
| Sodium Hydroxide | 0.05 |

| Ingredients | Weight Percent |
| --- | --- |
| Dimethicone[4] | 0.60 |
| Cyclomethicone/dimethiconal[5] | 0.50 |

1 Lucidol ® 75 from Elf Atochem, which is a powder containing 75% benzoyl peroxide active.
2 Carbopol ® 980 from B.F. Goodrich.
3 Pemulen ® TR-1 from B.F. Goodrich.
4 Dow Corning ® 200 Fluid (350 centistoke) from Dow Corning.
5 Dow Corning ® Q-2 1401 from Dow Corning.

In a suitable vessel a benzoyl peroxide slurry is prepared by combining the benzoyl peroxide with water which accounts for 3.6% of the batch. This slurry is passed through a Colloid or Urschel mill to disperse the benzoyl peroxide and the mill is rinsed through with an additional 1.44% of water. This rinse is added to the total slurry.

In a separate vessel a 5% sodium hydroxide solution is prepared with water to provide sodium hydroxide to the batch at 0.05%. In another vessel the carbomer 980 is gradually combined with an amount of water totaling 14.7% of the batch. It is added under agitation to disperse and hydrate the carbomer.

In a suitable mixing tank, the remaining water is added and heated to at least 75° C. In a separate vessel, the dimethicone, cetyl alcohol, stearyl alcohol, tocopherol acetate, glycerylhydroxy stearate, and steareth 100 are added and heated to at least 75° C. As the water phase is heating, the disodium EDTA, glydant plus, and alkyl alkylates are added and mixed until dissolved.

When both phases reach the required temperature, the oil phase is slowly added to the water phase while the entire batch is recycled through a tekmar mill to reduce the oil droplet particle size to approximately one to two microns. The batch is then cooled to room temperature under constant agitation.

When the batch has cooled, the carbopol slurry, benzoyl peroxide slurry, panthenol, allantoin and the cyclomethicone/dimethiconal is added. The batch is again recycled through the tekmar mill to disperse the materials. Finally, the 5% NaOH solution is gradually added with continuous mixing. The compositions is then mixed until homogeneous.

The resulting anti-acne composition exhibits low skin irritation and good physical and chemical stability, and is useful for topical application to human skin for the treatment of acne and other skin lesions.

EXAMPLE 4
Anti-Acne Gel

An anti-acne gel is prepared by combining the following ingredients using conventional mixing techniques.

| Ingredients | Weight Percent |
| --- | --- |
| Water | qs 100 |
| Benzoyl Peroxide[1] | 2.50 |
| Carbomer 980[2] | 0.30 |
| Glycerin | 3.00 |
| Glydant Plus | 0.20 |
| Acrylates/C10–30 Alkylacrylates crosspolymer[3] | 0.05 |
| Disodium EDTA | 0.10 |
| Tocopherol Acetate | 1.00 |
| Stearyl Alcohol | 2.25 |
| Cetyl Alcohol | 2.25 |
| Glycerylhydroxy Stearate | 0.74 |
| Steareth 100 | 0.50 |
| Dexpanthenol | 5.00 |

| Ingredients | Weight Percent |
| --- | --- |
| Sodium Hydroxide | 0.05 |
| Dimethicone[4] | 0.60 |
| Cyclomethicone/dimethiconal[5] | 0.50 |

1 Lucidol ® 75 from Elf Atochem, which is a powder containing 75% benzoyl peroxide active.
2 Carbopol ® 980 from B.F. Goodrich.
3 Pemulen ® TR-1 from B.F. Goodrich.
4 Dow Corning ® 200 Fluid (350 centistoke) from Dow Corning.
5 Dow Corning ® Q-2 1401 from Dow Corning.

In a suitable vessel a benzoyl peroxide slurry is prepared by combining the benzoyl peroxide with water which accounts for 3.6% of the batch. This slurry is passed through a Colloid or Urschel mill to disperse the benzoyl peroxide and the mill is rinsed through with an additional 1.44% of water. This rinse is added to the total slurry.

In a separate vessel a 5% sodium hydroxide solution is prepared with water to provide sodium hydroxide to the batch at 0.05%. In another vessel the carbomer 980 is gradually combined with an amount of water totaling 14.7% of the batch. It is added under agitation to disperse and hydrate the carbomer.

In a suitable mixing tank, the remaining water and glycerin are added and heated to at least 75° C. In a separate vessel, the dimethicone, tocopherol acetate, cetyl alcohol, stearyl alcohol, glycerylhydroxy stearate, and steareth 100 are added and heated to at least 75° C. As the water phase is heating, the disodium EDTA, glydant plus, and alkyl alkylates are added and mixed until dissolved.

When both phases reach the required temperature, the oil phase is slowly added to the water phase while the entire batch is recycled through a tekmar mill to reduce the oil droplet particle size to approximately one to two microns. The batch is then cooled to room temperature under constant agitation.

When the batch has cooled, the carbopol slurry, benzoyl peroxide slurry, dexpanthenol and the cyclomethicone/ dimethiconal is added. The batch is again recycled through the tekmar mill to disperse the materials. Finally, the 5% NaOH solution is gradually added with continuous mixing. The compositions is then mixed until homogeneous.

The resulting anti-acne composition exhibits low skin irritation and good physical and chemical stability, and is useful for topical application to human skin for the treatment of acne and other skin lesions.

EXAMPLE 5
Anti-Acne Gel

An anti-acne gel is prepared by combining the following ingredients using conventional mixing techniques.

| Ingredients | Weight Percent |
| --- | --- |
| Water | qs 100 |
| Benzoyl Peroxide[1] | 2.50 |
| Carbomer 980[2] | 0.30 |
| Glydant Plus | 0.20 |
| Acrylates/C10–30 Alkylacrylates crosspolymer[3] | 0.05 |
| Disodium EDTA | 0.10 |
| Stearyl Alcohol | 2.25 |
| Cetyl Alcohol | 2.25 |
| Glycerylhydroxy Stearate | 0.74 |
| Steareth 100 | 0.50 |
| Zinc Oxide | 1.00 |
| Sodium Hydroxide | 0.05 |
| Dimethicone[4] | 0.60 |

| Ingredients | Weight Percent |
| --- | --- |
| Cyclomethicone/dimethiconal[5] | 0.50 |

[1] Lucidol ® 75 from Elf Atochem, which is a powder containing 75% benzoyl peroxide active.
[2] Carbopol ® 980 from B.F. Goodrich.
[3] Pemulen ® TR-1 from B.F. Goodrich.
[4] Dow Corning ® 200 Fluid (350 centistoke) from Dow Corning.
[5] Dow Corning ® Q-2 1401 from Dow Corning.

In a suitable vessel a benzoyl peroxide slurry is prepared by combining the benzoyl peroxide with water which accounts for 3.6% of the batch. This slurry is passed through a Colloid or Urschel mill to disperse the benzoyl peroxide and the mill is rinsed through with an additional 1.44% of water. This rinse is added to the total slurry.

In a separate vessel a 5% sodium hydroxide solution is prepared with water to provide sodium hydroxide to the batch at 0.05%. In another vessel the carbomer 980 is gradually combined with an amount of water totaling 14.7% of the batch. It is added under agitation to disperse and hydrate the carbomer.

In a suitable mixing tank, the remaining water is added and heated to at least 75° C. In a separate vessel, the dimethicone, cetyl alcohol, stearyl alcohol, glycerylhydroxy stearate, and steareth 100 are added and heated to at least 75° C. As the water phase is heating, the disodium EDTA, glydant plus, and alkyl alkylates are added and mixed until dissolved.

When both phases reach the required temperature, the oil phase is slowly added to the water phase while the entire batch is recycled through a tekmar mill to reduce the oil droplet particle size to approximately one to two microns. The batch is then cooled to room temperature under constant agitation.

When the batch has cooled, the carbopol slurry and the cyclomethicone/dimethiconal is added. The batch is again recycled through the tekmar mill to disperse the materials. Finally, half of the 5% NaOH solution is gradually added with continuous mixing. The benzoyl peroxide slurry is then added to the mixture. The other half of the sodium hydroxide is then added. The composition is then mixed until homogeneous.

The resulting anti-acne composition exhibits low skin irritation and good physical and chemical stability, and is useful for topical application to human skin for the treatment of acne and other skin lesions.

EXAMPLE 6

Anti-Acne Gel

An anti-acne gel is prepared by combining the following ingredients using conventional mixing techniques.

| Ingredients | Weight Percent |
| --- | --- |
| Water | qs 100 |
| Benzoyl Peroxide[1] | 2.50 |
| Carbomer 980[2] | 0.30 |
| Glydant Plus | 0.20 |
| Acrylates/C10–30 Alkylacrylates crosspolymer[3] | 0.05 |
| Disodium EDTA | 0.10 |
| Stearyl Alcohol | 2.25 |
| Cetyl Alcohol | 2.25 |
| Glycerylhydroxy Stearate | 0.74 |
| Steareth 100 | 0.50 |
| Dexpanthenol | 5.00 |
| Zinc Oxide | 1.00 |
| Sodium Hydroxide | 0.05 |
| Dimethicone[4] | 0.60 |
| Cyctomethicone/dimethiconal[5] | 0.50 |

[1] Lucidol ® 75 from Elf Atochem, which is a powder containing 75% benzoyl peroxide active.
[2] Carbopol ® 980 from B.F. Goodrich.
[3] Pemuten ® TR-1 from B.F. Goodrich.
[4] Dow Corning ® 200 Fluid (350 centistoke) from Dow Corning.
[5] Dow Corning ® Q-2 1401 from Dow Corning.

In a suitable vessel a benzoyl peroxide slurry is prepared by combining the benzoyl peroxide with water which accounts for 3.6% of the batch. This slurry is passed through a Colloid or Urschel mill to disperse the benzoyl peroxide and the mill is rinsed through with an additional 1.44% of water. This rinse is added to the total slurry.

In a separate vessel a 5% sodium hydroxide solution is prepared with water to provide sodium hydroxide to the batch at 0.05%. In another vessel the carbomer 980 is gradually combined with an amount of water totaling 14.7% of the batch. It is added under agitation to disperse and hydrate the carbomer.

In a suitable mixing tank, the remaining water is added and heated to at least 75° C. In a separate vessel, the dimethicone, cetyl alcohol, stearyl alcohol, glycerylhydroxy stearate, and steareth 100 are added and heated to at least 75° C. As the water phase is heating, the disodium EDTA, glydant plus, and alkyl alkylates are added and mixed until dissolved.

When both phases reach the required temperature, the oil phase is slowly added to the water phase while the entire batch is recycled through a tekmar mill to reduce the oil droplet particle size to approximately one to two microns. The batch is then cooled to room temperature under constant agitation.

When the batch has cooled, the carbopol slurry, dexpanthenol and the cyclomethicone/dimethiconal are added. The batch is again recycled through the tekmar mill to disperse the materials. Finally, half of the 5% NaOH solution is gradually added with continuous mixing. The benzoyl peroxide slurry is then added to the mixture. The other half of the sodium hydroxide is then added. The composition is then mixed until homogeneous.

The resulting anti-acne composition exhibits low skin irritation and good physical and chemical stability, and is useful for topical application to human skin for the treatment of acne and other skin lesions.

What is claimed is:

1. A dermatological composition for treating skin lesions wherein the skin lesions is acne, seborrhea, burns, varicose ulcers, or sycosis vulgaris comprising:
    (a) from about 2.5% to about 10% of benzoyl peroxide,
    (b) from about 0.1% to about 10% of a compound for reducing the skin irritation associated with the benzoyl peroxide selected from the group consisting of tocopherol, C1–C30 carboxylic acid esters of tocopherol, and mixtures thereof, and (c) a topical carrier.

2. A composition according to claim 1 wherein the concentration of benzoyl peroxide is from about 2.5% to about 5% and wherein the concentration of the compound for reducing the skin irritation associated with the benzoyl peroxide is from about 0.5% to about 5%.

3. A composition according to claim 1 wherein said compound for reducing the skin irritation associated with benzoyl peroxide is tocopherol.

4. A composition according to claim 1 wherein said compound for reducing the skin irritation associated with benzoyl peroxide is a C1–C30 carboxylic acid ester of tocopherol.

5. A method of treating skin lesions wherein the skin lesions is acne, seborrhea, burns, varicose ulcers, or sycosis vulgaris in humans comprising topically applying to a human in need of treatment a safe and effective amount of a composition comprising:

(a) from about 2.5% to about 10% of benzoyl peroxide, (b) from about 0.1% to about 10% of a compound for reducing the skin irritation associated with the benzoyl peroxide selected from the group consisting of tocopherol, C1–C30 carboxylic acid esters of tocopherol, and mixtures thereof, and (c) a topical carrier.

6. A method according to claim 5 wherein the concentration of benzoyl peroxide is from about 2.5% to about 5% and wherein the concentration of the compound for reducing the skin irritation associated with the benzoyl peroxide is from about 0.5% to about 5%.

7. A method for reducing skin irritation associated with the treatment of skin lesions wherein the skin lesions is acne, seborrhea, burns, varicose ulcers, or sycosis vulgaris in a human by topically applying a composition comprising benzoyl peroxide, the method comprising topically applying to the skin lesions a composition comprising from about 2.5% to about 10% of benzoyl peroxide, from about 0.1% to about 10% of a compound for reducing the skin irritation associated with the benzoyl peroxide, the compound comprising tocopherol, a C1–C30 carboxylic acid ester of tocopherol, or mixtures thereof, and a topical carrier.

8. A method according to claim 7 wherein the concentration of benzoyl peroxide is from about 2.5% to about 5% and wherein the concentration of the compound for reducing the skin irritation associated with the benzoyl peroxide is from about 0.5% to about 5%.

9. A method according to claim 7, wherein the compound for reducing the skin irritation associated with the benzoyl peroxide is tocopherol.

10. A method according to claim 7, wherein the compound for reducing the skin irritation associated with the benzoyl peroxide is C1–C30 carboxylic acid ester of tocopherol.

* * * * *

UNITED STATES PATENT AND TRADEMARK OFFICE
CERTIFICATE OF CORRECTION

PATENT NO.     : 5,932,228

DATED          : August 3, 1999

INVENTOR(S)    : Bonnie Joy Hall et al.

It is certified that error appears in the above-identified patent and that said Letters Patent is hereby corrected as shown below:

At column 8, line 42 "*Technology.*" should read --*Technology,*--.

At column 10, line 64 "Glycerythydroxy" should read --Glycerylhydroxy--.

At column 16, line 6 "Cyctomethicone" should read --Cyclomethicone--.

At column 16, line 10 "Pemuten" should read --Pemulen--.

At column 16, line 52 "vulgaris comprising" should read --vulgaris, comprising--.

At column 18, line 21 "is C1-C30" should read --is a C1-C30--.

Signed and Sealed this

Twenty-eighth Day of March, 2000

Attest:

Q. TODD DICKINSON

*Attesting Officer*          *Commissioner of Patents and Trademarks*